United States Patent
Subramaniam

(10) Patent No.: US 9,339,262 B2
(45) Date of Patent: *May 17, 2016

(54) RETRACTOR WITH INTEGRATED LIGHT SOURCE

(71) Applicant: CLEAR SURGICAL LIMITED, Glasgow (GB)

(72) Inventor: Murali Subramaniam, Glasgow (GB)

(73) Assignee: CLEAR SURGICAL LIMITED, Glasgow (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/500,296

(22) Filed: Sep. 29, 2014

(65) Prior Publication Data

US 2015/0045627 A1 Feb. 12, 2015

Related U.S. Application Data

(63) Continuation of application No. 12/679,067, filed as application No. PCT/GB2008/050786 on Sep. 4, 2008, now Pat. No. 8,876,713.

(30) Foreign Application Priority Data

Sep. 19, 2007 (GB) .................................. 0718268.6

(51) Int. Cl.
*A61B 1/32* (2006.01)
*A61B 17/02* (2006.01)
(Continued)

(52) U.S. Cl.
CPC ......... *A61B 17/0206* (2013.01); *A61B 19/5202* (2013.01); *A61B 2017/00734* (2013.01); *A61B 2017/2837* (2013.01); *A61B 2019/4868* (2013.01); *A61B 2019/4878* (2013.01)

(58) Field of Classification Search
CPC ............... A61B 17/02; A61B 19/5202; A61B 2019/5206; A61B 2019/521
USPC .................................................. 600/184–246
See application file for complete search history.

(56) References Cited

U.S. PATENT DOCUMENTS 3,766,910 A 10/1973 Lake
4,226,228 A 10/1980 Shin et al.
(Continued)

FOREIGN PATENT DOCUMENTS

DE 202004005757 6/2004
DE 102006042985 4/2007
(Continued)

*Primary Examiner* — Mary Hoffman
(74) *Attorney, Agent, or Firm* — Allen, Dyer, Doppelt, Milbrath & Gilchrist, P.A.

(57) ABSTRACT

A surgical retractor that comprises an integrated light source for creating a working space for the access of dissecting instruments employed during an open surgical procedure is described. The retractor is of the type that comprises two elongated arms mechanically connected by a pivot that allows the retractor to move between a closed and an open configuration. The described retractors further comprise adjustable paddle assemblies located at the distal end of the elongated arms and a unique locking mechanism that allows for the relative separation of the paddle assemblies to be set at any position between the closed and open configuration of the retractor. The design of the retractor provides them with increased functionality while allowing them to be cost effectively produced so that they can simply be disposed of after use.

16 Claims, 14 Drawing Sheets

(51) Int. Cl.
*A61B 19/00* (2006.01)
*A61B 17/00* (2006.01)
*A61B 17/28* (2006.01)

(56) References Cited

U.S. PATENT DOCUMENTS

| | | | |
|---|---|---|---|
| 4,502,485 | A | 3/1985 | Burgin |
| 4,562,832 | A | 1/1986 | Wilder et al. |
| 5,005,108 | A | 4/1991 | Pristash et al. |
| 5,035,232 | A | 7/1991 | Lutze et al. |
| 5,503,617 | A | 4/1996 | Jako |
| 5,569,300 | A | 10/1996 | Redmon |
| 5,871,493 | A | 2/1999 | Sjostrom et al. |
| 5,944,736 | A | 8/1999 | Taylor et al. |
| 6,080,105 | A | 6/2000 | Spears |
| 6,185,356 | B1 | 2/2001 | Parker et al. |
| 6,224,545 | B1 | 5/2001 | Cocchia et al. |
| 6,504,985 | B2 | 1/2003 | Parker et al. |
| 6,554,768 | B1 | 4/2003 | Leonard |
| 6,602,189 | B1 | 8/2003 | Bennetti et al. |
| 8,088,066 | B2 | 1/2012 | Grey et al. |
| 8,137,284 | B2 | 3/2012 | Miles et al. |
| 8,435,175 | B2 | 5/2013 | McMahon et al. |
| 2003/0060686 | A1 | 3/2003 | Taylor et al. |
| 2003/0095781 | A1 | 5/2003 | Williams |
| 2004/0024291 | A1 | 2/2004 | Zinkel |
| 2004/0242971 | A1 | 12/2004 | Holland et al. |
| 2005/0096646 | A1 | 5/2005 | Wellman et al. |
| 2005/0154263 | A1 | 7/2005 | Nady |
| 2006/0217596 | A1 | 9/2006 | Wiliams |
| 2007/0060795 | A1 | 3/2007 | Vayser et al. |
| 2007/0244353 | A1 | 10/2007 | Larsen |
| 2007/0293729 | A1 | 12/2007 | Grey et al. |
| 2008/0108877 | A1 | 5/2008 | Bayat |
| 2008/0114207 | A1 | 5/2008 | Krupa et al. |
| 2008/0234549 | A1 | 9/2008 | Geist et al. |
| 2008/0269565 | A1 | 10/2008 | McMahon et al. |
| 2009/0018399 | A1 | 1/2009 | Martinelli et al. |
| 2009/0187078 | A1 | 7/2009 | Dunlop |
| 2011/0144439 | A1 | 6/2011 | Miles et al. |
| 2012/0041268 | A1 | 2/2012 | Grey et al. |
| 2012/0116170 | A1 | 5/2012 | Vayser et al. |
| 2012/0149992 | A1 | 6/2012 | Duggal et al. |
| 2012/0209076 | A2 | 8/2012 | Hahn et al. |
| 2012/0209080 | A1 | 8/2012 | Grey et al. |
| 2012/0238822 | A1 | 9/2012 | Miles et al. |

FOREIGN PATENT DOCUMENTS

| | | |
|---|---|---|
| GB | 1381387 | 1/1975 |
| WO | 2005102177 | 11/2005 |

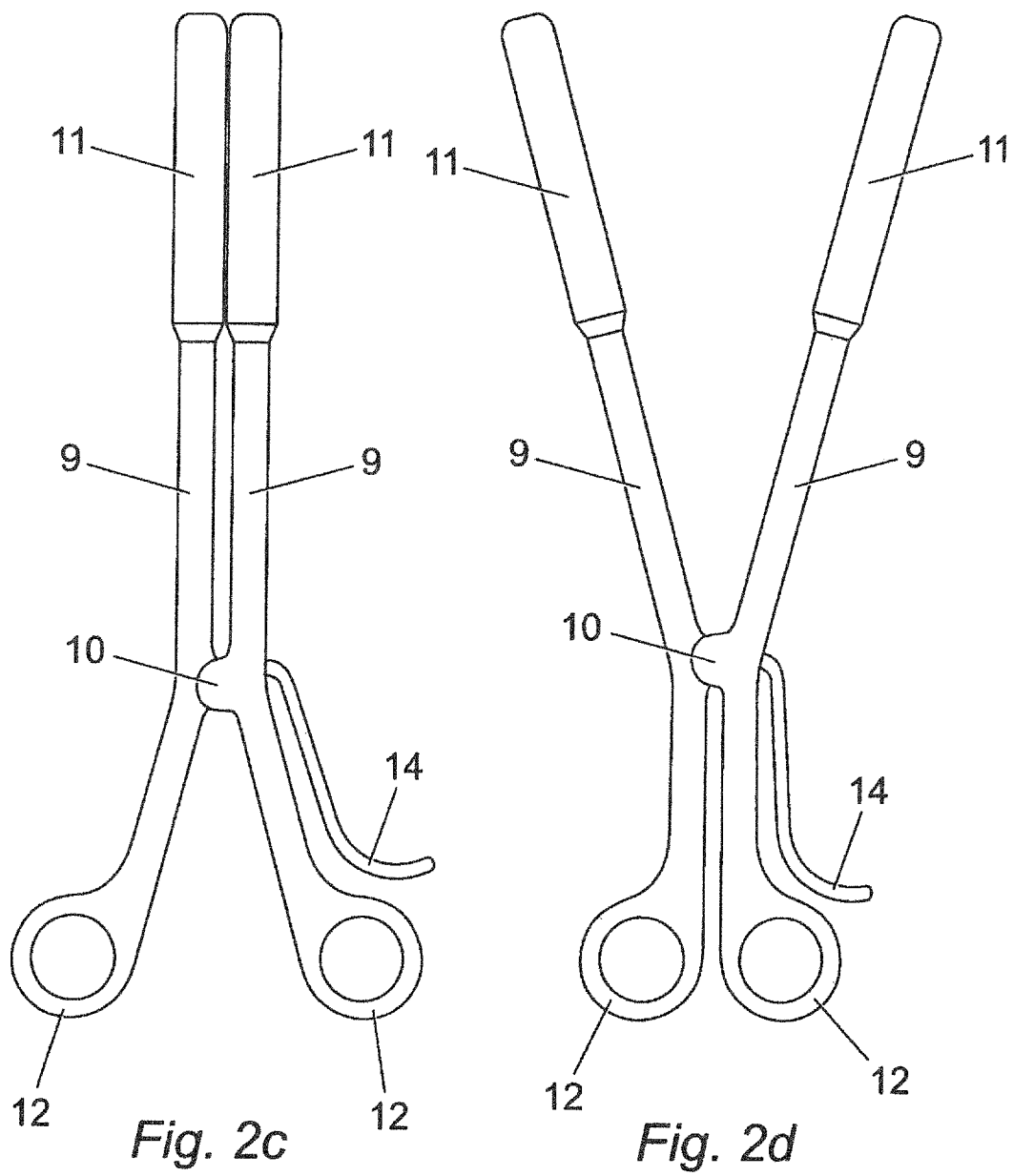

RETRACTOR WITH INTEGRATED LIGHT SOURCE

The present invention relates to the field of surgical retractors and, in particular, to a surgical retractor that comprises an integrated light source for creating a working space for the access of dissecting instruments employed during an open surgical procedure. Such open surgical procedures include cholecystectomy operations or other types of procedures which require the retraction of tissue at a relatively deep location within the body of a patient.

A retractor is a surgical instrument that separates the edges of a surgical incision or wound, and holds back underlying organs and tissues, so that body parts under the incision may be accessed. They are available in many shapes, sizes, and styles.

Figure 1:
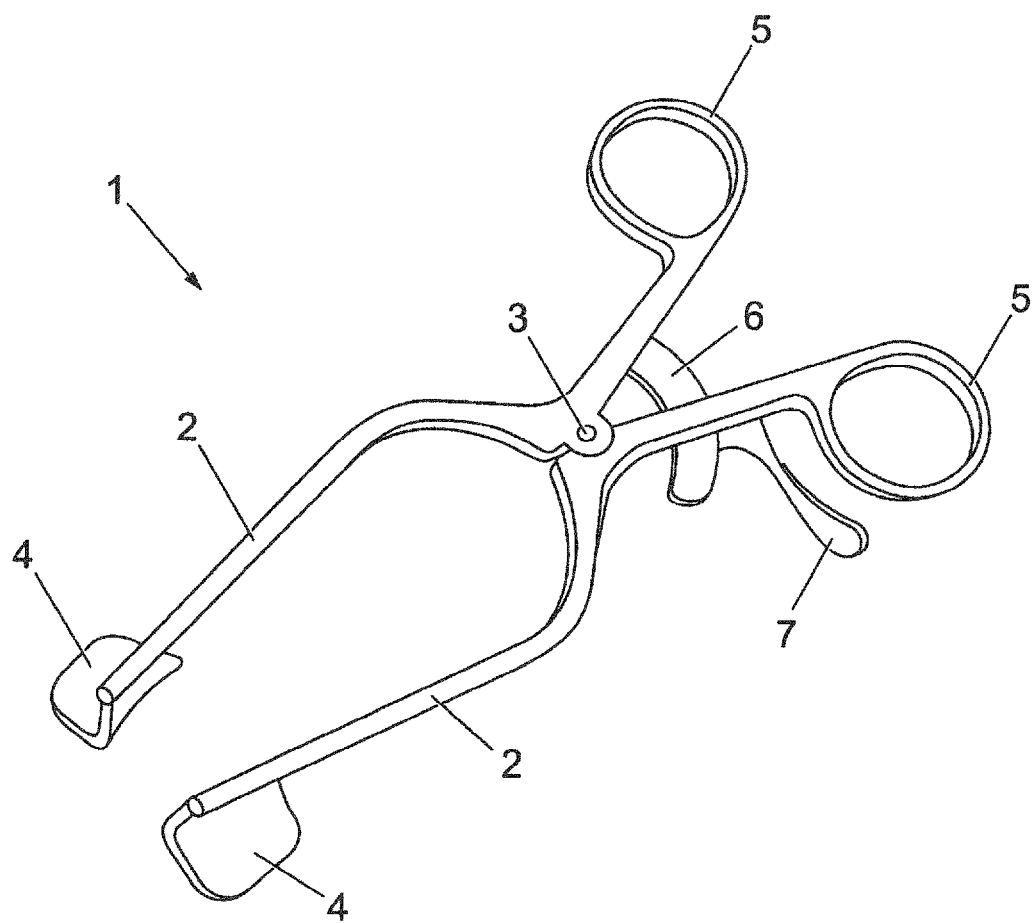

One retractor design commonly employed within open surgical procedures is presented within FIG. 1, generally depicted by reference numeral 1. The retractor 1 is of a type comprising two elongated arms 2 mechanically connected by a pivot 3. At the distal end of each elongated arm 2 is located a paddle 4. The separation of the paddles 4 is achieved through the manual manipulation of handles 5 located at the proximal end of the elongated arms 2, in conjunction with the operation of a ratchet 6. When required to be moved between these predetermined positions the surgeon depresses a lever 7 which acts to release the ratchet 6 and thus allow the elongated arms 2 to pivot relative to each other.

When employed for open surgery the retractor 1 generally require the employment of a source of illumination so as to provide the necessary illumination of the workspace created. Currently, a surgeon must use a separate light source such as a head-mounted light or a separate light generating instrument so as to illuminate the workspace. When a head-mounted light is used and the surgical site is located deep within the body of the patient, it is often difficult to view the desired tissue without shadows forming from adjacent tissue, or from the surgeon himself. Since the available tissue opening is relatively limited, it is desirable that the number, and size of instruments employed, be kept to a minimum. Therefore, the use of a separate light generating instrument is not a satisfactory solution to the shadowing problems experienced through the deployment of head-mounted lights. It is therefore desirable to provide a source of light inside the retracted tissue area to illuminate the tissue of interest without obstructing the view, or hindering the manual dexterity, of the surgeon.

A further drawback of the design of the retractor 1 resides in the fact that the ratchet 6 only allows the paddles 4 to be locked in a number of predetermined positions, as defined by the number of ratchet teeth. In order to increase the flexibility in the positioning of the paddles 4 it would be advantageous to have a releasable locking mechanism that does not lock in a stepwise continuous manner.

Generally, the retractors 1 are machined from stainless steel so as provide them with the required mechanical strength and to allow then to withstand thousands of cycles of use. Inclusive within the use cycle is the need for the sterilisation of the retractor 1, typically through the employment of an autoclave. As is known to those skilled in the art, sterilisation processes are expensive and, if not carried out correctly, can lead to cross contamination between patients. It would therefore be advantageous to the health of patients, and to reducing the costs involved in open surgery, if the reliance on the need for sterilisation of the retractors 1 could be reduced.

It is an object of the present invention to obviate or mitigate at least one of the foregoing disadvantages of the retractors known to those skilled in the art.

SUMMARY OF INVENTION

According to a first aspect of the present invention there is provided a retractor suitable for creating a working space for open surgery, wherein the retractor comprises two elongated arms mechanically connected by a pivot that allows the retractor to move between a closed and an open configuration, and a paddle assembly located at the distal end of each of the elongated arms, wherein at least one of the paddle assemblies comprises a light source for illumination of the working space.

By employing such a retractor a surgeon significantly reduces the problematic feature of shadowing within the working space as is associated with the use of head mounted light sources. Furthermore, the requirement for a separate light generating instrument is also removed thus resulting in a less cluttered working space for the surgeon.

Preferably, at least one of the elongate arms comprises a housing adapted to house a first power source for the light source. Preferably, the housing is capable of forming a seal. Advantageously the housing is capable of forming a hermetic seal.

Being able to form a seal, and preferably a hermetic seal, allows electronics, power sources and the like to be housed within the retractor without risk of contamination etc. and also permitting sterilisation such as ethylene oxide sterilisation to be carried out.

Preferably, the retractor comprises a switch adapted to selectively illuminate the light source. Preferably and advantageously the switch comprises a non contact switching mechanism. Preferably the switching mechanism is located within the housing. Optionally the switch comprises a reed switch adapted to open when a magnet is removed from proximity thereto.

Having a non contact switching mechanism allows the retractor light source to be switched on without the need for access to the switch itself. It may therefore be housed internally which is beneficial from a hygienic point of view.

Preferably, the housing comprises a plurality of struts arranged substantially transverse to the length of the elongate arm. These struts lend structural rigidity to the arm. Preferably, the struts comprise recesses adapted to locate the first power source and a conducting means adapted to conduct electricity from the first power source to the light source.

Optionally the at least one paddle assembly is detachably mounted to the distal end of the elongated arm.

Preferably the at least one paddle assembly comprises a casing within which is housed an extractible paddle. The incorporation of an extractible paddle allows the surgeon to vary the size of the retractor so increasing the flexibility of the device.

Preferably the light source is mounted within the paddle assembly such that a normal to the light source forms an acute angle with a substantially planar first surface of the paddle. This arrangement has the effect of directing the light down into the working space.

Optionally the paddle assembly further comprises a second power source housed within the casing wherein the second power source provides the required current to illuminate the light source.

Optionally the distal end of the elongated arm comprises a conductive insert such that when the paddle assembly is mounted on the distal end of the elongated arm the conductive insert electrically connects the first or second power sources to the light source. Such an arrangement removes the requirement for a separate on/off switch to be incorporated within the retractor.

Preferably the retractor further comprises handles located at the proximal ends of each of the elongated arms.

Optionally, the power source is housed within one or more of the retractor handles.

Most preferably the retractor further comprises a locking mechanism, the locking mechanism comprising a lever arranged to mechanically communicate with a unidirectional clutch arranged to prevent the retractor from moving towards the closed configuration. Such an arrangement provides a locking mechanism that prevents the retractor from closing without the surgeon releasing the unidirectional clutch by manually pulling on the lever. Furthermore, the locking mechanism allows for the relative separation of the paddle assemblies to be set at any position between the closed and open configuration of the retractor.

Preferably the unidirectional clutch comprises a wrap spring clutch.

Most preferably the handles and the elongated members comprise glass-filled nylon. Most preferably the at least one paddle assembly comprise a sparked translucent polycarbonate. Sparked translucent polycarbonate acts to mask the internal components of the paddle assembly while allowing for the generated light to exit the assembly, as required. The employment of such materials significantly reduces the costs involved in the production of the retractor, thus making it commercially viable to be employed for single use operation. As a result, the requirement for sterilisation of the retractor is significantly reduced.

Most preferably both paddle assemblies comprises a light source. Employing two light source results in an increased level of illumination for the working space.

SPECIFIC DESCRIPTION

Figure 2A:
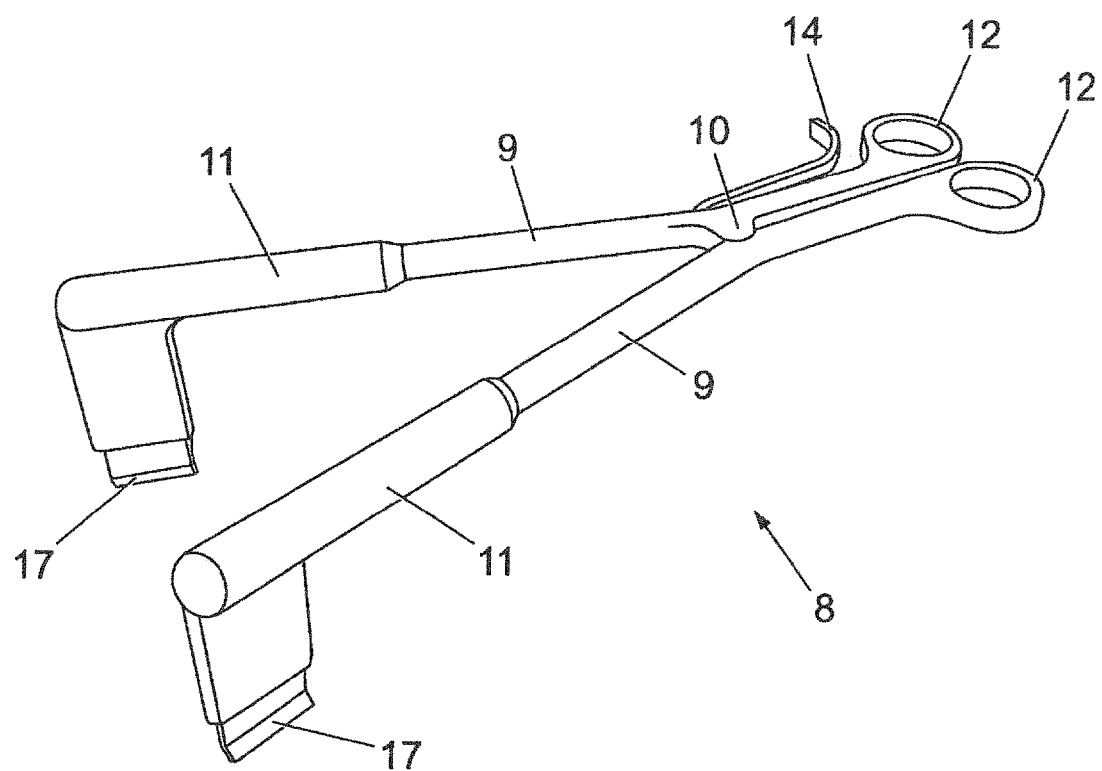
Figure 2B:
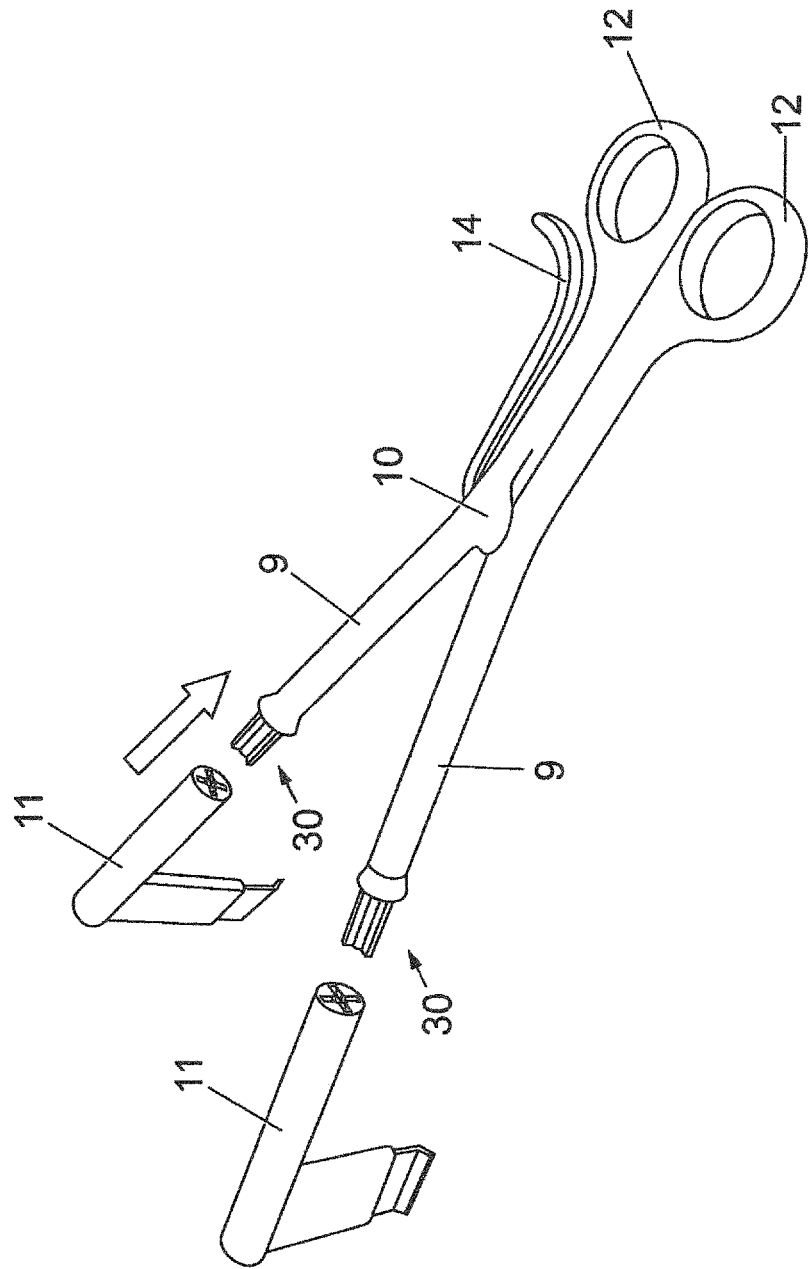
Figure 3:
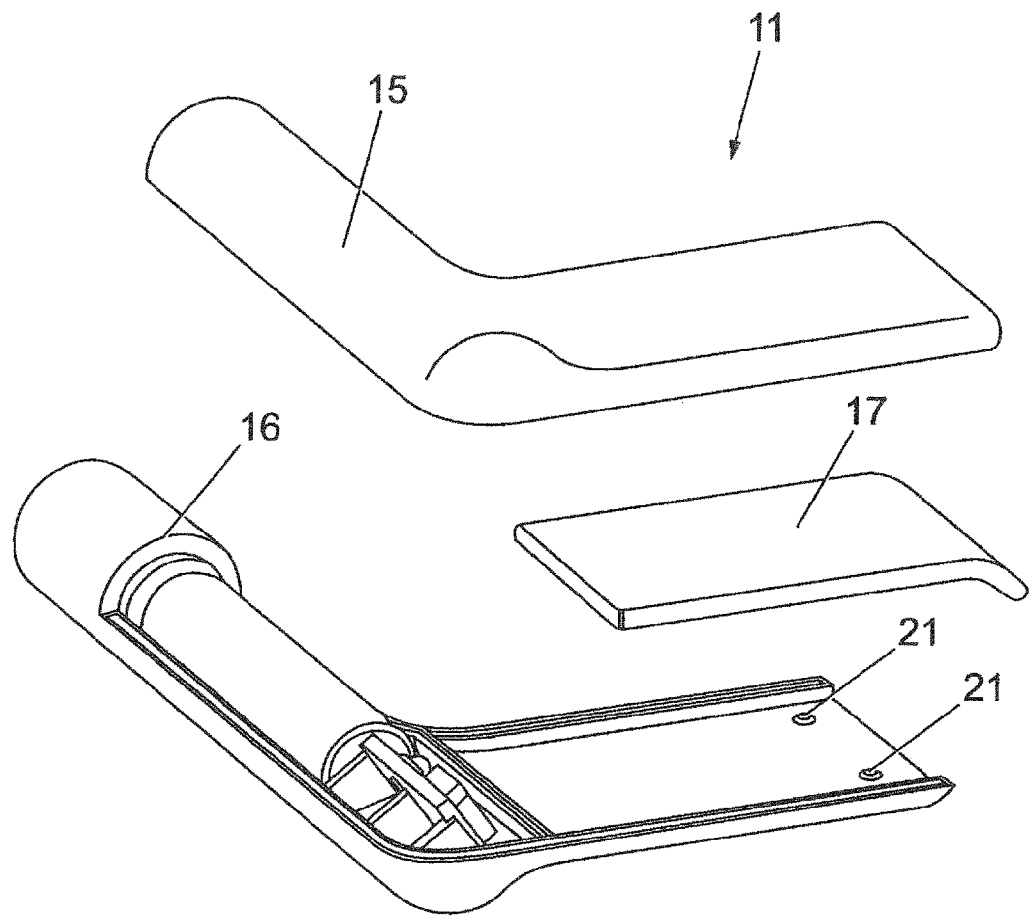
Figure 4:
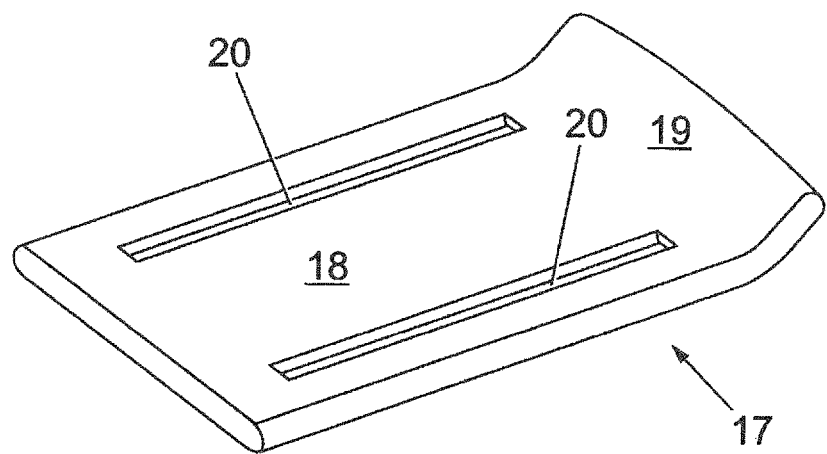
Figure 5:
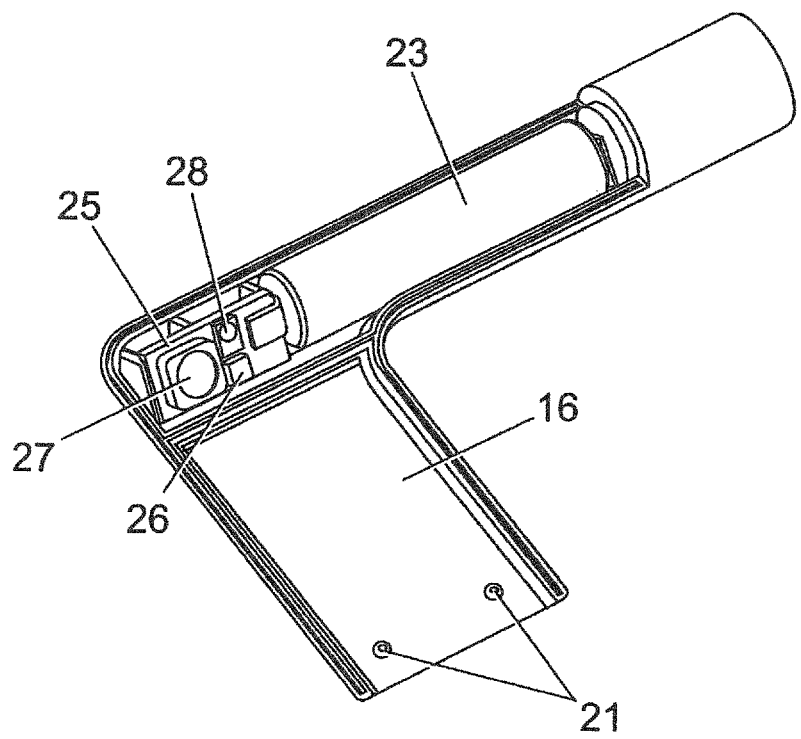
Figure 6:
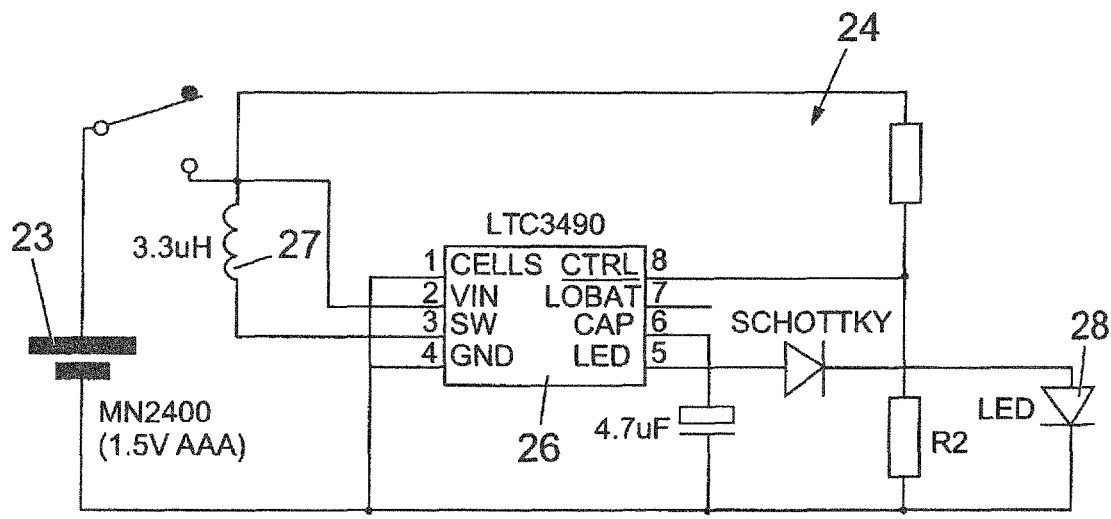
Figure 7:
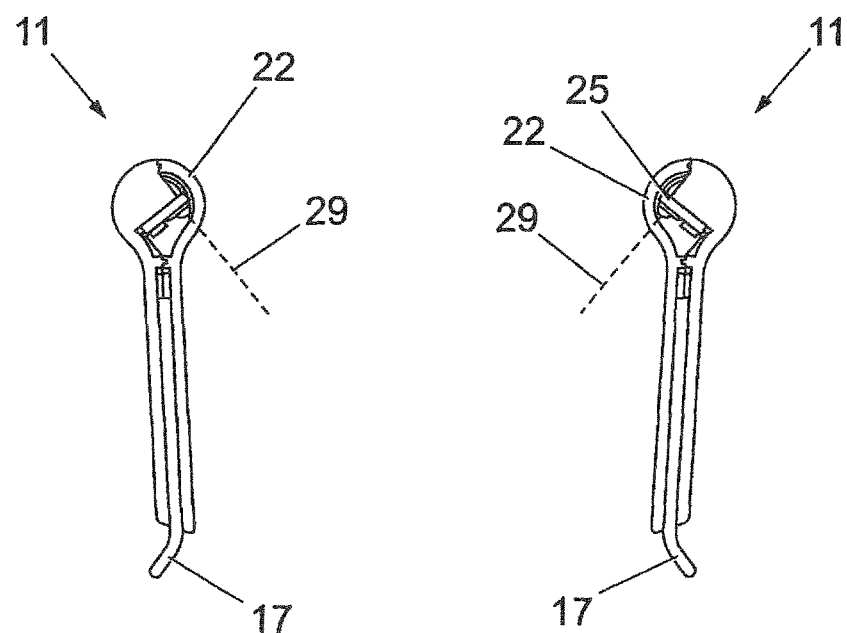
Figure 8:
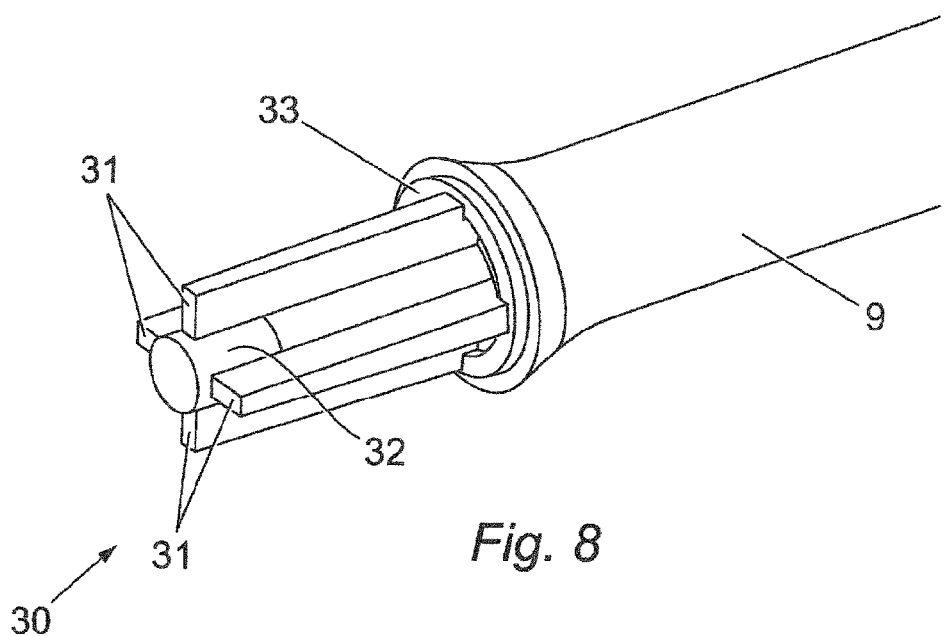
Figure 9:
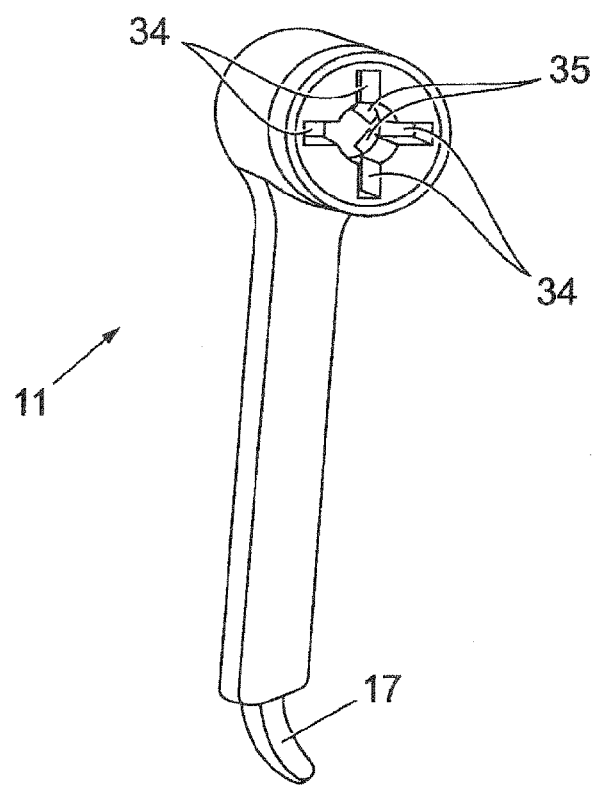
Figure 10:
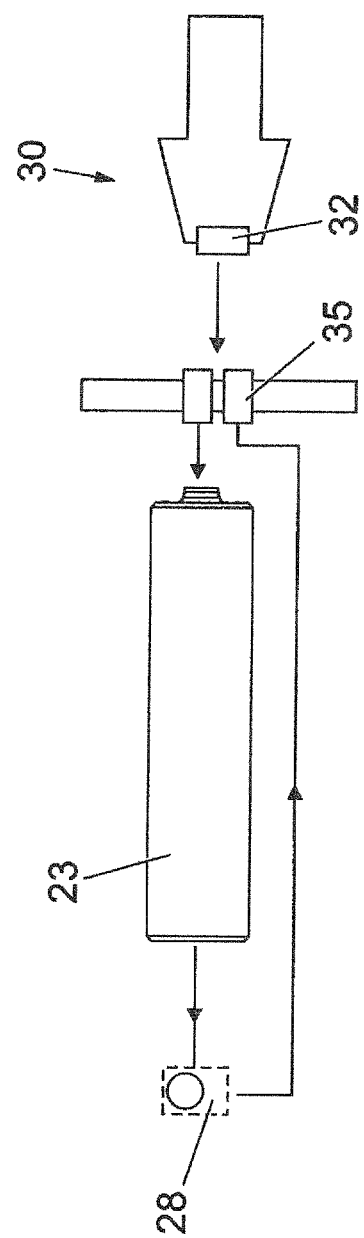
Figure 11:
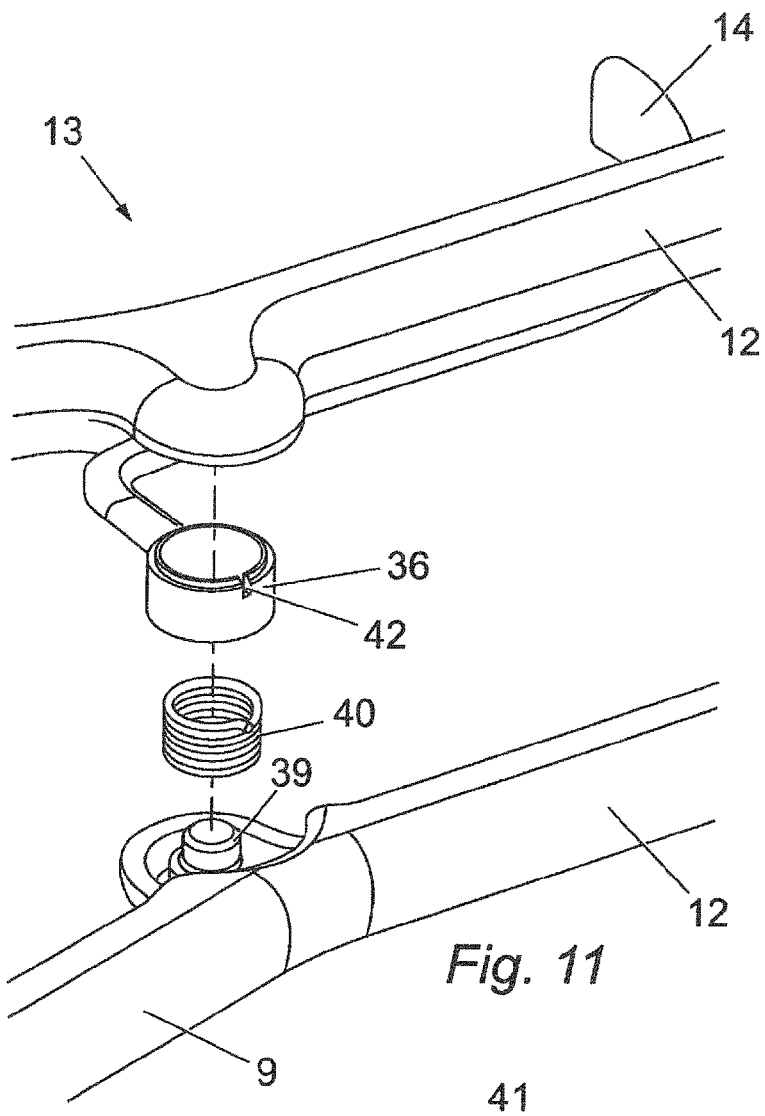
Figure 12:
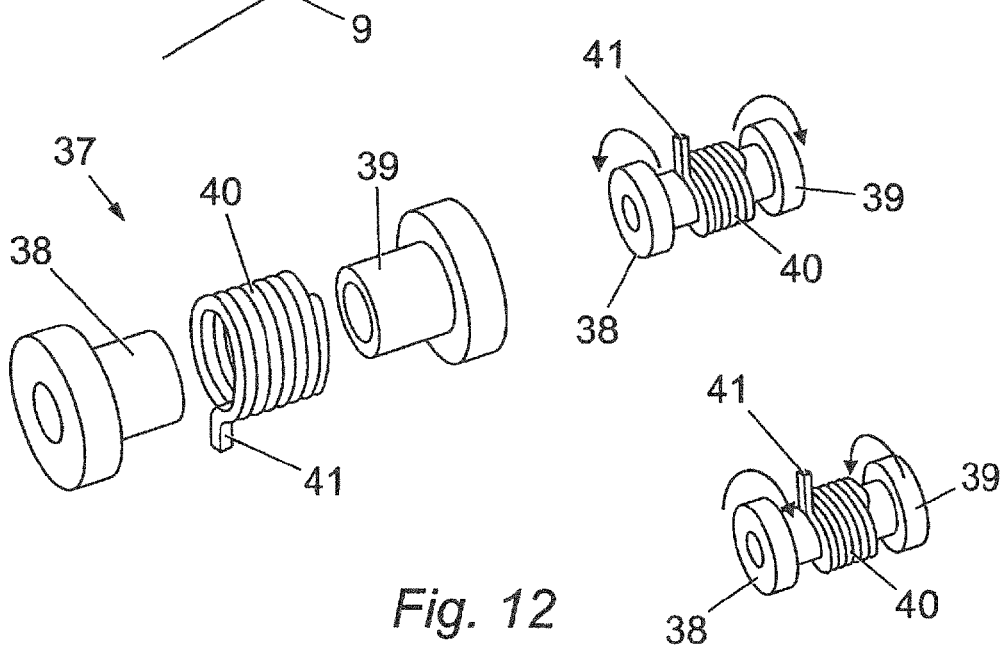
Figure 13:
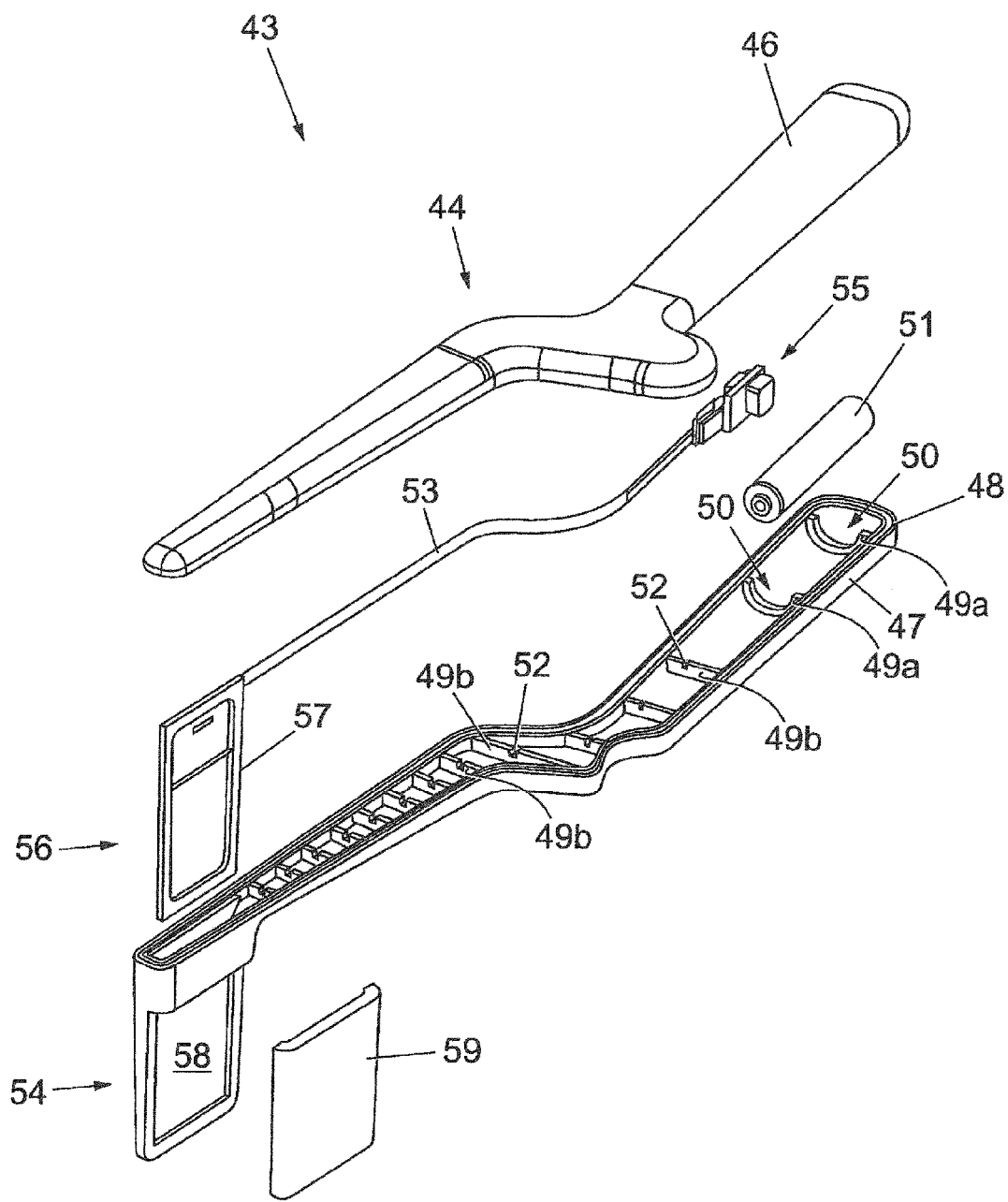
Figure 14:
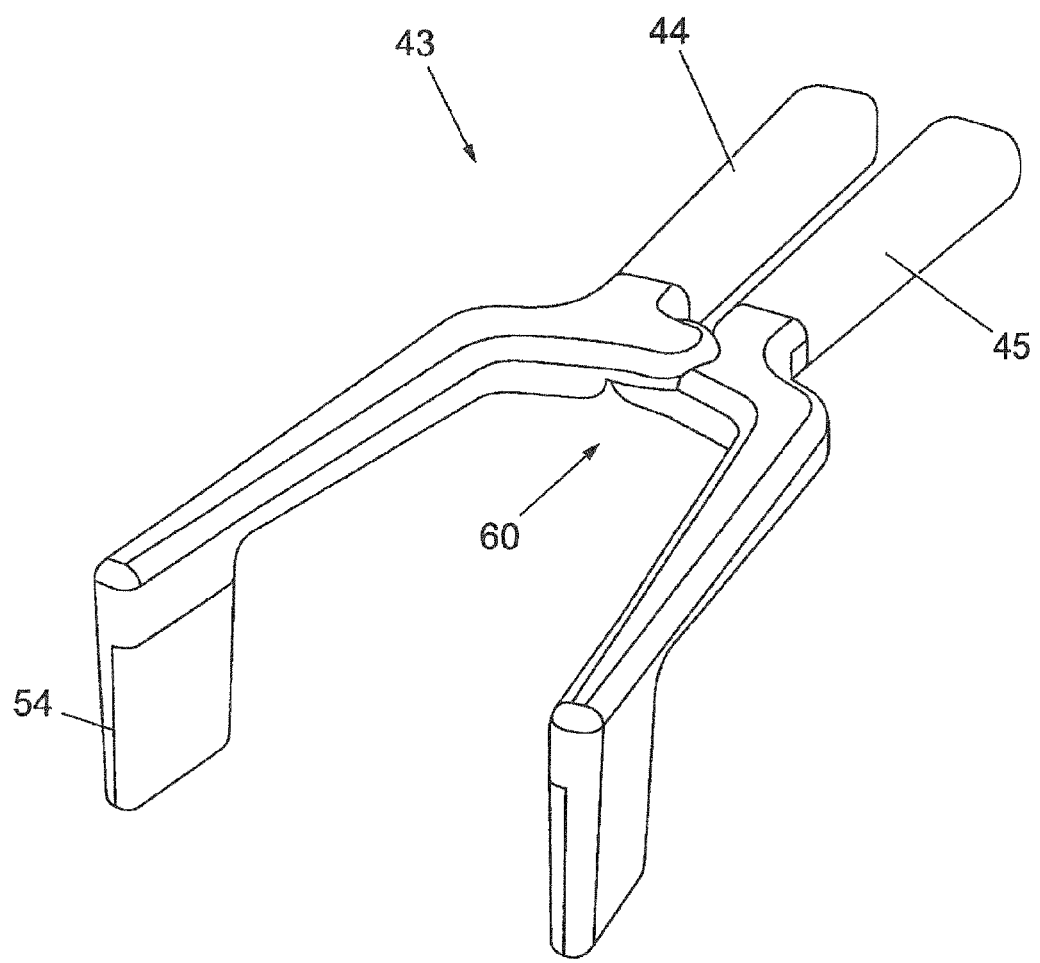
Figure 15:
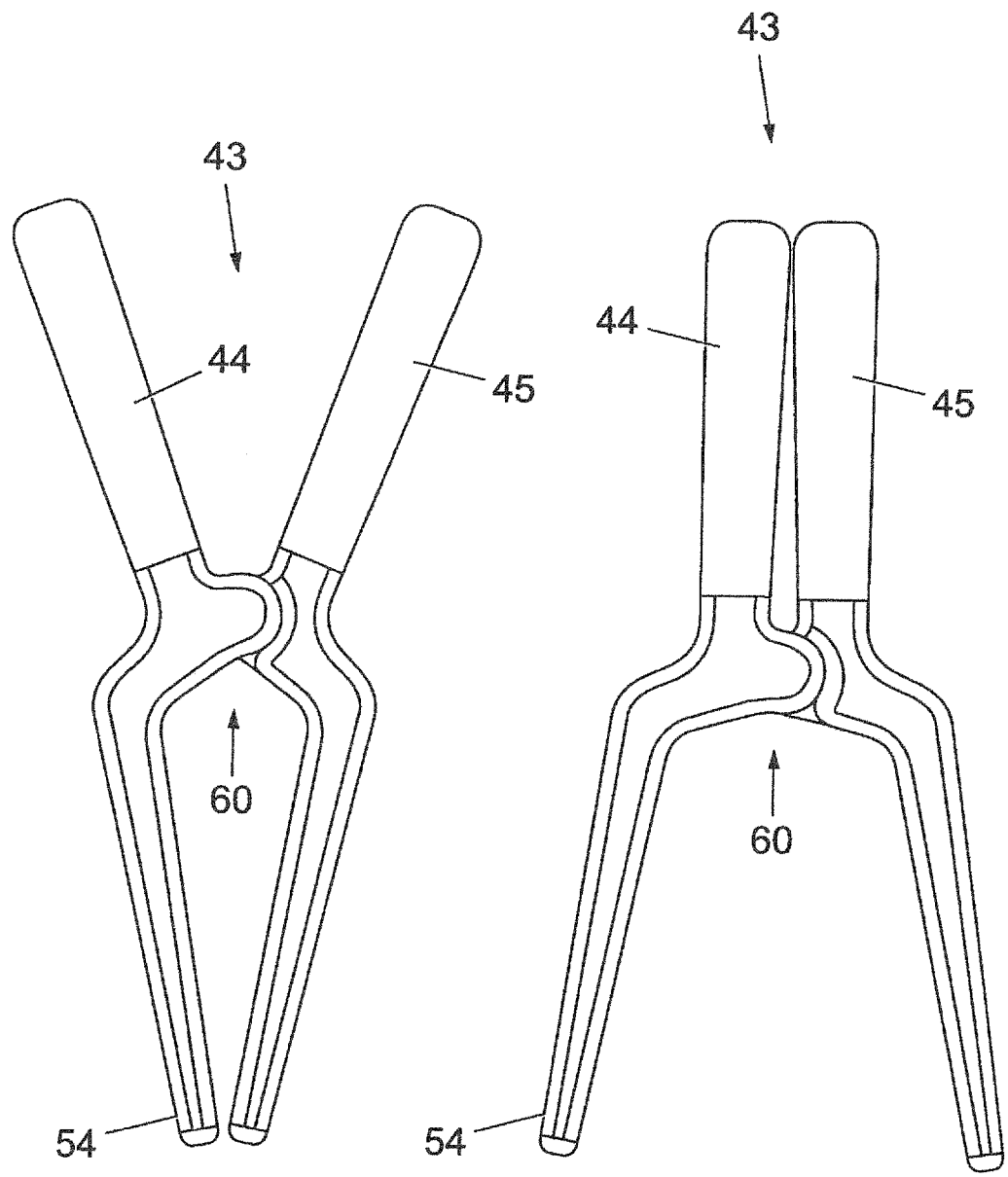
Figure 16:
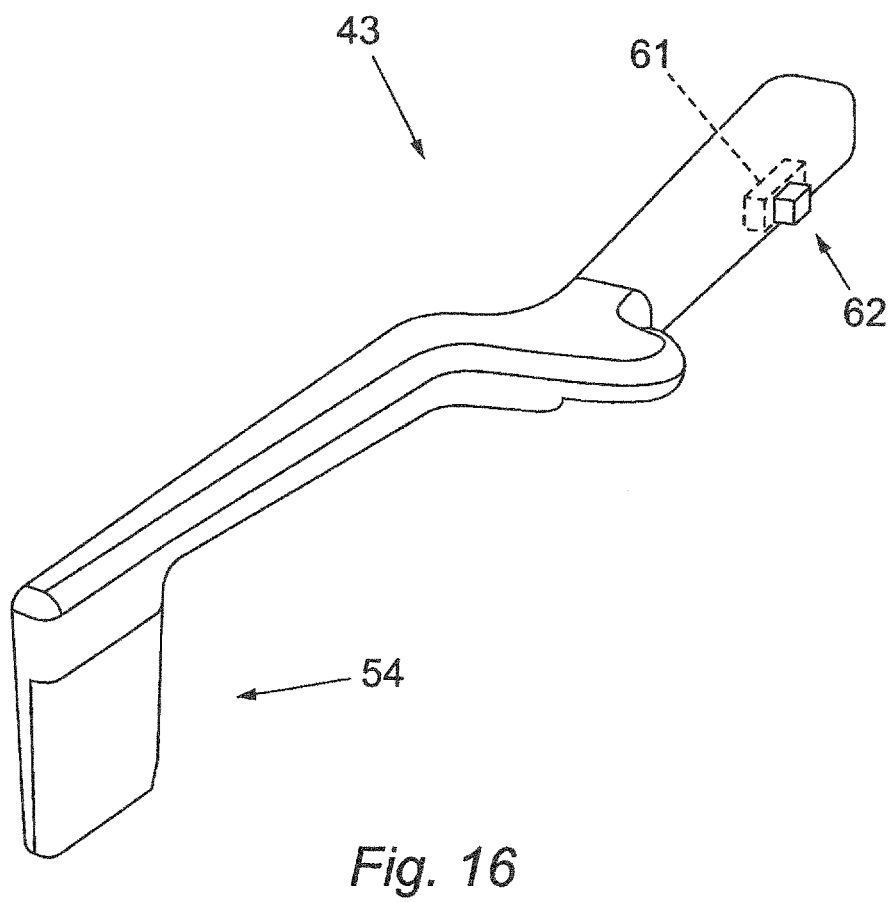

Embodiments of the present invention will now be described, by way of example, with reference to the accompanying drawings, in which:

FIG. 1 presents a prior art surgical retractor commonly employed within open surgical procedures;

FIG. 2 presents a:
(a) perspective view;
(b) an exploded perspective view;
(c) a top view of a closed position; and
(d) a top view of an open position, of a surgical retractor in accordance with an aspect of the present invention;

FIG. 3 presents an exploded view of a paddle assembly of the surgical retractor of FIG. 2;

FIG. 4 presents a perspective view of paddle of the surgical retractor of FIG. 2;

FIG. 5 presents a perspective view of the paddle assembly of FIG. 3 with a first case section and the paddle removed;

FIG. 6 presents a circuit diagram of the illumination electronics of the retractor;

FIG. 7 presents cross sectional end views of two paddle assemblies;

FIG. 8 presents a perspective view of a distal end of an elongated arm or the retractor;

FIG. 9 presents a perspective view of a socket of the paddle assembly configured to receive the distal end of FIG. 8;

FIG. 10 present a schematic representation of the circuit formed from when the socket of FIG. 9 receives the distal end of the elongated arm of FIG. 8;

FIG. 11 presents an exploded view of the locking mechanism of the retractor of FIG. 2;

FIG. 12 presents an exploded view and two operational views of a unidirectional clutch employed by the locking mechanism of FIG. 11;

FIG. 13 presents an exploded view of an alternative surgical retractor in accordance with an aspect of the present invention;

FIG. 14 presents a perspective view of the alternative surgical retractor of FIG. 13;

FIG. 15 presents a plan view of the alternative surgical retractor of FIG. 13 in:
(a) a closed position; and
(b) an open position; and FIG. 16 presents a perspective view of a further alternative elongate arm similar to that illustrated in FIG. 13.

For consistency and clarity purposes the various features of the described retractors are referred to by the same reference numerals throughout the specification. Where appropriate, those reference numerals employed to describe the features common to alternative embodiments of the invention are also maintained within the specific description.

DETAILED DESCRIPTION

In order to assist understanding of the present invention, FIG. 2 presents various views of a surgical retractor 8 in accordance with an aspect of the present invention. In particular, FIG. 2 presents a perspective view, an exploded perspective view, a top view of a closed position and a top view of an open position of the retractor 8. The retractor 8 is again of a type comprising two elongated arms 9 mechanically connected by a pivot 10. At the distal end of each elongated arm 9 is located a paddle assembly 11, the separation of the paddle assemblies 11 being controlled through the manual manipulation of handles 12 located at the proximal end of the elongated arms 9, in conjunction with the operation of a locking mechanism 13 which moves between a closed and open position via the controlled operation of a lever 14, further detail of which is described below. From FIG. 2(b) it can be seen that the paddle assemblies 11 comprise independent units which snap fit onto the distal ends of the elongated arms 9, further detail of which is also provided below.

Detail of the components of the paddle assembly 11 can be seen from the exploded view presented within FIG. 3. The paddle assembly 11 comprises an hermetically sealed unit consisting of a first case section 15, a second case section 16 and a paddle 17 located between the first and second casing sections, 15 and 16, respectively. The hermetic seal of paddle assembly 11 is created by ultrasonic welding the first 15 and second casing sections 16. Such a process has the advantage of eliminating the need for any fixtures or sealing gaskets.

FIG. 4 presents a perspective view of the paddle 17 which can be seen to comprise a substantially planar first surface 18 and a curved second surface 19 arranged to project out of the plane of the first surface 18. Located one side of the first surface 18 are two elongated grooves or runners 20 which form an interference fit with two corresponding pips 21 located on an internal surface of the second casing section 16. As a result of this arrangement the protrusion of the paddle 17 from the casing can be quickly and easily adjusted so as to allow a surgeon to alter the size of the retractor 8 depending on the depth of the incision (or in other words the amount of skin, fat and muscle that has to be retracted). The interference fit between the pips 21 and the runners 20 is such that the paddle 17 can not fall out when the paddle assembly 11 is held vertically, but can be pulled out of, or pushed into the casing by the surgeon. In its fully retracted position, the paddle 17 is approximately 45 mm long, extending to approximately 80 mm in its fully extended configuration.

Further detail of the paddle assembly 11 can be seen from FIG. 5 within which is presented a perspective view of the paddle assembly with the first casing section 15 and the paddle 17 removed. Located within a cylindrical chamber 22 is a battery 23 employed to power illumination electronics 24 of the retractor 8.

A circuit diagram of the illumination electronics 24 is provided within FIG. 6. The illumination electronics 24 can be seen to comprise a printed circuit board (PCB) 25 upon which is located a driver 26 and an inductor 27 employed to regulate a current drawn from the battery 23 so as to power a white LED 28. In the presently described embodiment, the LED comprises a high powered Luxeon Rebel device, powered by a AAA battery. As a result the combined effect of the inductor 27 and the driver 26 is to provide a 50 mA current to the LED 28 thus providing approximately four hours worth of light generation.

The orientation of the LEDs 28 relative to the elongated arms 9 of the retractor 8 can be seen from the cross sectional end views of the paddle assemblies 11 presented within FIG. 7. The PCB 25 with associated LED 28 and illumination electronics 26 and 27 are mounted such that they are angled relative to the first surface 18 of the associated paddle 17 when both components are located within the paddle assembly 11. In practice, the LED 28 is mounted such that its normal 29 forms an acute angle relative to the substantially planer first surface 18 of the paddle 17. Accordingly, light generated by the LEDs 28 propagates in a generally downwards direction into the created working space when the retractor 8 is deployed by a surgeon. This has the effect of providing flood lighting to the working space formed within a patient.

It should be noted that the basic configuration of the paddle assemblies 11 allows for the working space to be fully illuminated without requiring the employment of any special lenses or further inserts. The overall effect is a general illumination of the working space, with the spread being defined by a particular type of LED employed.

A significant advantage of the presently described retractor 8 can be seen from an examination of FIGS. 8 to 10. FIG. 8 presents a perspective view of a distal end of an elongated arm 9 of the retractor 8, generally depicted by reference numeral 30. The distal end 30 can be seen to comprise four radially orientated guides 31, located at the centre of which is a conductive insert 32. At the proximal end of the four guides 31 is located an O-ring 33. The distal end therefore comprises a male plug for the elongated arm.

A corresponding female socket is located at one end of the cylindrical chamber 22. The female socket comprises four grooves 34, suitable for receiving the four guides 31 of the male plug, and two metal contacts 35 moulded within a central area of the female socket.

The incorporation of the male plug and the female socket provides a novel method for activating the LED 28, details of which can be seen from FIG. 10. In particular, FIG. 10 presents a schematic representation of a circuit formed when the paddle assembly 11 is snap-fitted onto an elongated arm 9. When the snap-fit action takes place, the conductive insert 32 completes a circuit comprising the battery 23, the LED 28 and the two metal contacts 35. This allows current to flow from the battery 23 to the LED 28, thus activating the generation of light. At the same time the O-ring 33 provides a seal for the respective paddle assembly 11.

One significant advantages of employing such a design within the retractor 8 is that it removes the requirement to have a dedicated on/off switch within the retractor 8. Not having such a switch improves the simplicity of the apparatus. It is known to those skilled in the art that on/off switches are historically difficult to seal since most switches involve a moving element that runs from outside, to inside, a casing which can lead to leak paths.

It will be readily apparent to those skilled in the art that alternative designs along a similar theme may be incorporated within the retractor 8. For example, the conductive insert could be replaced by a magnet such that it activates a reed switch located within the female socket when the paddle assembly 11 is snap-fitted onto the elongated arm 9. Such an embodiment would further reduce the risk of a leak path forming since no components would be required to run from inside, to outside, the casing.

In a further alternative embodiment, a flexible diaphragm maybe located within the female socket such that it is depressed when the male plug, located at the distal end 30 of the elongated arm 9, is snap-fitted into the socket. This would result in a sprung connector moving towards the battery 23, thus completing the circuit, as required.

A further advantage of the presently described retractor 8 resides in the locking mechanism 13 employed by the device, details of which is provided within FIGS. 11 and 12. In particular, FIG. 11 presents an exploded view of the locking mechanism 13 which can be seen to comprise lever 14, a ring like end 36 of which surrounds an unidirectional clutch 37. FIG. 12 presents an exploded view, and two operational views, of the unidirectional clutch 37.

The unidirectional clutch 37 is in the form of a wrap spring clutch, itself comprising a first 38 and second hub 39, about which is located a helical spring 40. The inner diameter of the spring 40 is such that it forms an interference fit with the outer diameter of the first 38 and second hubs 39. Positioned at one end of the spring 40 is a tang 41 which locates within a recess 42 formed within the ring like end 36 of the lever 14. As a result there exists direct mechanical communication between the lever 14 and the spring 40.

With the above described arrangement, any attempt to rotate either the first 38 or second hub 39, in the direction of the helix, forces the spring 40 to wrap down around the hubs 38 and 39 thus immediately preventing their relative rotation. However, rotation is possible if the hubs 38 and 39 are rotated in the direction opposite to the helix of the spring 40.

Within the locking mechanism 13 the spring 40 is configured such that when the retractor 8 is moved towards its open position, see FIG. 2(d), the hubs, 38 and 39, rotate in the opposite direction to the direction of the helix. As a result, the spring 40 does not prevent the opening of the retractor 8. However, the retractor 8 can not immediately be moved towards the closed position of FIG. 2(c) because to do so requires the hubs, 38 and 39, to rotate in the direction of the helix. When it is desired to close the retractor 8 the lever 14 is pulled by the surgeon towards the handle 12. This movement acts to rotate the spring 40 in the direction opposite to the helix so releasing the hubs 38 and 39 from the spring 40. As a result, the hubs, 38 and 39, are now free to rotate in the direction of the helix and so the retractor 8 can be moved to the closed position of FIG. 2(c).

The above described locking mechanism 13 provides the retractor 8 with a smooth acting, integrated indexing system, that is hidden from view of the surgeon and allows for a continuous number of paddle separation positions to be set.

It will be readily apparent that a number of alternative features may be employed within the retractor 8. For example, various alternative batteries may be employed within an appropriately sized chamber 22, e.g. "coin cell" batteries.

Similarly alternative coloured LEDs may also be employed. In a further alternative, the light source may be in the form of a thin panel, mounted on the external surface of the front casing section 15.

A yet further alternative embodiment would be for the retractor to comprise only one paddle assembly with an integrated light source. The second paddle assembly could either be fixed to one of the elongated arms or alternatively be snap fitted thereon in a similar manner to that previously described. It is recognised however that such embodiments would experience a reduced level of illumination of the working space.

The principle materials involved in the production of the retractor 8 is glass-filled nylon for all but the paddle assemblies 11. The paddle assemblies 11 are made from sparked translucent polycarbonates. These materials are employed primarily for their stiffness. However, the sparking of the polycarbonates provides them with a frosted effect which, to a large degree, acts to hide the contained electronics but allows for the generated light to propagate so illuminating the working space, as required.

The employment of such materials significantly reduces the costs involved in the production of the retractor 8, thus providing a rugged apparatus for a cost which makes it suitable for single use operation. As a result, the requirement for sterilisation of the device is removed following use since the retractor 8 is intended to be used for a single operation only.

The snap-fit activation of the LEDs 28 provides the retractor 8 with approximately four hours of illumination. This is found to be more than adequate for the majority of operations for which it would be deployed. A further advantage of employing LEDs 28 is that they generate effectively cold light which is a highly desirable feature of any retractor 8 employed within open surgery.

Finally, the incorporation of retractable paddles provides the retractor 8 with enhanced flexibility when compared with those retractors known in the prior art.

From the above description it can be seen that the retractor 8 is ideally suited to be provided within a sterile package. Once opened, the surgeon simply snap-fits the paddle assemblies 11 onto the end of the elongated arms 9, thus activating the light and commencing the lifetime of the device. The paddle length is then selected and the device deployed as appropriate. Following completion of the operation, or the loss of power from the battery 23, the retractor 8 is simply disposed of.

An alternative embodiment of the present invention is now described with further reference to FIGS. 13 to 16. FIGS. 13 and 14 show perspective views of the component parts of an alternative retractor 43. With particular reference to FIG. 13, an exploded view of a first elongate arm 44 of the retractor 43 is shown, and FIGS. 14 and 15 show the first elongate arm 44 in an assembled form and arranged with its corresponding second elongate arm 45 and ready for use as a retractor 43.

The arm 44 can be seen to comprise a top casing section 46 and a bottom casing section 47 which engage by way of a shaped groove 48 extending around a perimeter of the bottom casing section 47 and a corresponding ridge (not visible) extending around a perimeter of the top casing section 46.

A number of lateral struts 49 extend across the width of the arm 44 lending structural rigidity to the arm 44 as well as providing a means of arranging and locating internal components therein. For example, the two lowermost struts 49A incorporate semi-circular recesses 50 which accommodate a battery 51. Other struts (for example 49B) incorporate thinner channels 52 which accommodate and guide a conductive strip 53. Housing the battery 51 at this end of the elongate arm 44 makes the retractor 43 easier to handle.

The conductive strip 53 serves to conduct electricity from the battery 51 at one end of the arm 44 to a paddle 54 at the opposite end. A switch 55 is located at the battery end of the conductive strip 53 and allows a user to selectively illuminate light source 56 as and when required, typically when in use. The light source 56 comprises a frame 57 which is inserted into a corresponding recess 58 in the paddle 54, and a shaped transparent window 59 which permits light from the light source 56 to illuminate the surrounding area.

FIGS. 14 and 15 show the first elongate arm 44 assembled and connected to second elongate arm 45 at a hinge section 60 to form a retractor 43. Within the hinge section 60 is located a unidirectional clutch 37 as illustrated and exemplified with reference to FIGS. 11 and 12 above. FIG. 15(a) shows the retractor 43 in a closed position and FIG. 15(b) shows the retractor 43 in an open position such as that in which it will be used.

In an alternative embodiment, see the partial view in FIG. 16, the switch shown in FIG. 13 is replaced with a reed switch 61 which resides entirely within the casing. A magnet 62 may be placed on the outer surface of the casing in a position which holds the reed switch 61 open, and when the retractor 43 is to be used the magnet 62 is removed, causing the reed switch 61 to close thus switching on the light source within the paddle (s) 54. This embodiment has particular advantages, especially in terms of hygiene and sterilisation. As the switch mechanism (as well as any other electronics) can be entirely housed within the retractor casing, the retractor can be hermetically sealed. Thus, processes such as ethylene oxide (EO) sterilisation, which is a common way of sterilising medical supplies and implements, can be carried out on the retractor.

The foregoing description of the invention has been presented for the purpose of illustration and description, and is not intended to be exhaustive or to limit the invention to the precise form disclosed. The described embodiments were chosen and described in order to best explain the principals of the invention and its practical applications, to thereby enable others skilled in the art to best utilise the invention in various embodiments and with various modifications as are suited to the particular use upon completion. Therefore, further modifications and improvements may be incorporated without departing from the scope of the appended claims.

The invention claimed is:

1. A retractor suitable for creating a working space for open surgery, the retractor comprising:
    two elongated arms mechanically connected to each other by a pivot that allows the retractor to move between a closed and an open configuration;
    each elongated arm comprising a paddle assembly located at a distal end, wherein
    a first paddle assembly comprises a transparent window and forms a hermetically sealed housing for a first light source and a first power source for the first light source, the first light source being mounted within the first paddle assembly and configured to illuminate the working space.

2. A retractor as claimed in claim 1 further comprising a switch adapted to selectively illuminate the first light source.

3. A retractor as claimed in claim 2 wherein the switch comprises a non contact switching mechanism.

4. A retractor as claimed in claim 3 wherein the switching mechanism is located within the first paddle assembly.

5. A retractor as claimed in claim 2 wherein the switch comprises a reed switch adapted to open when a magnet is removed from proximity thereto.

6. A retractor as claimed in claim 1 wherein the first elongated arm comprises a plurality of struts arranged substantially transverse to a length of the first elongated arm.

7. A retractor as claimed in claim 1 wherein the first light source is mounted within the first paddle assembly such that a normal to the first light source forms an acute angle with a substantially planar first surface of the paddle assembly.

8. A retractor as claimed in claim 1 wherein the retractor further comprises a locking mechanism, the locking mechanism comprising a lever arranged to mechanically communicate with a unidirectional clutch arranged to prevent the retractor from moving towards the closed configuration.

9. A retractor as claimed in claim 8 wherein the unidirectional clutch comprises a wrap spring clutch.

10. A retractor as claimed in claim 1 wherein the retractor further comprises handles located at the proximal ends of the two elongated arms.

11. A retractor as claimed in claim 10 wherein the first and second handles comprise glass filled nylon.

12. A retractor as claimed in claim 1 wherein the two elongated arms comprise glass filled nylon.

13. A retractor as claimed claim 1 wherein the transparent window of the first paddle assembly comprises a sparked translucent polycarbonate.

14. A retractor as claimed in claim 1 wherein a second paddle assembly comprises a second transparent window and forms a second hermetically sealed housing for a second light source and a second power source for the second light source, the second light source being mounted within the second paddle assembly and configured to illuminate the working space.

15. A retractor as claimed in claim 1 wherein the light source is in the form of a panel.

16. A retractor suitable for creating a working space for open surgery, the retractor comprising:
    two elongated arms mechanically connected to each other by a pivot that allows the retractor to move between a closed and an open configuration;
    handles located at the proximal ends of the two elongated arms;
    the two arms each comprising a paddle assembly located at a distal end, wherein
    each paddle assembly comprises a transparent window and forms a hermetically sealed housing for a light source and a power source for the light source, the light sources being mounted within the respective paddle assemblies and configured to illuminate the working space.

* * * * *